United States Patent [19]
Fredrickson

[11] Patent Number: 6,117,844
[45] Date of Patent: Sep. 12, 2000

[54] METHOD AND COMPOSITION FOR ANTIVIRAL THERAPY

[75] Inventor: William R. Fredrickson, Indianapolis, Ind.

[73] Assignee: F&S Group, Inc., Pacific Palisades, Calif.

[21] Appl. No.: 08/668,324

[22] Filed: Jun. 26, 1996

Related U.S. Application Data

[63] Continuation of application No. 08/335,138, Nov. 7, 1994, abandoned.

[51] Int. Cl.$^7$ ............................ A61K 31/70; A61K 31/35
[52] U.S. Cl. ............................................... 514/27; 514/460
[58] Field of Search ........................................ 514/460, 27

[56] References Cited

U.S. PATENT DOCUMENTS

| | | | |
|---|---|---|---|
| 3,033,877 | 5/1962 | Veer et al. | 260/345.8 |
| 3,737,550 | 6/1973 | Nook et al. | 424/279 |
| 3,786,068 | 1/1974 | Kelly | 260/340.5 |
| 3,793,346 | 2/1974 | Kelly | 260/340.5 |

FOREIGN PATENT DOCUMENTS

| | | |
|---|---|---|
| 683957 | 2/1969 | South Africa . |

OTHER PUBLICATIONS

Renis, Antimicro Agent Chemotherapy, 1969 pp. 167–172, 970.
Walter et al Appl Micro vol 26(5) pp 773–76, 1973.
Hirschman, Noter vol 238 Aug. 20, 1972, pp. 277–79, 1972.
"The Bitter Glucoside of the Olive", W.V. Cruess and C. L. Alsberg, *J. Am. Chem. Soc.* 56:2115–2117 (1934).
Isolation of a Bacterial Inhibitor from Green Olives, Fleming, et al., *Applied Microbiology*, vol. 18, No. 5, pp856–860 (1969).
"Preparation of Antimicrobial Compounds by Hydrolysis of Oleuropein from Green Olives", Walter et al., *Applied Microbiology*, vol. 26, No. 5, pp773–776 (1973).
"Antimicrobial Properties of Oleuropein and Products of Its Hydrolysis from Green Olives", Fleming et al., *Applied Microbiology*, vol. 26, No. 5, pp777–782 (1973).
"In Vitro Antiviral Activity of Calcium Elenolate", Harold Renis, *Antimicrobial Agents and Chemotherapy*, 1969 (printed 1970) pp. 167–172.
"Inactivation of DNA Polymerases of Murine Leukaemia Viruses by Calcium Elenolate" S. Z. Hirschman, *Nature (New Biology)*, 238: 277–279 (1972).
"Antiviral Activity of Calcium Elenolate on Parainfluenza Infection of Hamsters", M. G. Soret, *Antimicrobial Agents and Chemotherapy*, 1969 (printed 1970) pp. 160–166.

"Preliminary Safety Studies with Calcium Elenolate, an Antiviral Agent", Elliot et al., *Antimicrobial Agents and Chemotherapy*, 1969 (printed 1970) pp. 173–176.
"Binding of Eugenol and O–ethoxybenzoic Acid to Bovine Serum Albumin", S. Fujisawa and E. Masuhara, *J. Dent. Res.*, vol. 60, No. 4, pp. 860–864 (1981).
"Pharmacological Analysis of the Iridoid Oleuropein," V. Petkov and P. Manolov, *Drug Res.*, 22(9) pp. 1476–1486 (1972).
"A Multichemical Defense Mechanism of Bitter Olive *Olea Europaea* (Oleaceae)", Kubo et al. *J. of Chemical Ecology*, vol. 11, No. 2, pp. 251–263 (1985).
"Secoiridoids from *Olea Europaea*", Gariboldi, et al., *Phytochem.* 25(4) pp. 865–869 (1986).
"Inactivation of Myxoviruses by Calcium Elenolate", Harold Renis, *Antimicrobial Agents and Chemotherapy*, vol. 8, No. 2 pp. 194–199 (1975).
"Conversion of Secologanin into Elenolic Acid and 18–Oxayohimban Alkaloids", R. T. Brown et al, *J. of Chem. Soc. Perkin Trans.* vol. 1, pp160–162 (1976).
"Mulluscicides from Olive *Olea europaea* and Their Efficient Isolation by Countercurrent Chromatographies", I. Kubo and A. Matsumoto, *J. Agric. Food Chem.*, vol. 32, No. 3 pp 687–688 (1984).
"HPLC Analysis of Oleuropein and Some Flavonoids in Leaf and Bud of *Olea Europaea* L.", P. Ficarra and R. Ficarra, *IL Farmaco*, vol. 46, No. 6, pp. 803–815 (1991).
"A New Secoiridoid from Olive Wastewaters", R. L. Scalzo and M. L. Scarpati, *Journal of Natural Products*, vol. 56, No. 4, pp. 621–623 (1993).
"Leaf Extract of *Olea eropea* Rich in Oleuropeine, Products from It, Their Application as Medicines and Compositions Containing Them", G. Combes and A. Escaut, *Chem Abstracts*, vol. 98: 221797r (1983).
"(—)–Elenolic Acid Esters", Takano et al., *Chem Abstracts*, vol. 106: 67534c (1987).
"Preparation of Dihydropyran Derivative as Antiviral Agents and Precursors for Alkyl (—)–Elenolates", Takano et al., *Chem Abstracts*, vol. 113: 58936c (1990).
"Structure and Stereochemistry of Elenolic Acid", MacKellar et al., *J. Am. Chem. Soc.* vol. 95 (21) pp. 7155–7156 (1973).

*Primary Examiner*—Russell Travers
*Attorney, Agent, or Firm*—Barnes & Thornburg

[57] ABSTRACT

A method of treatment of diseases of viral origin is disclosed. The method comprises oral or parenteral administration of an antiviral amount of a naturally occurring secoiridoid from plants of the family Oleaceae or derivatives thereof. Preferred oral dosage forms include the secoiridoid oleuropein in pure form or as a component of dried plant material of *Olea europaea* or a dried extract thereof and a pharmaceutically acceptable carrier.

3 Claims, No Drawings

METHOD AND COMPOSITION FOR ANTIVIRAL THERAPY

This Application is a continuation of application Ser. No. 08/335/138 filed Nov. 7, 1994 now abandoned.

FIELD OF THE INVENTION

This invention relates to treatment of disease of viral origin in warm-blooded vertebrates. More particularly, this invention is directed to the use of secoiridoid compounds naturally occurring in plants of the family Oleaceae and derivatives thereof.

BACKGROUND AND SUMMARY OF THE INVENTION

The olive tree and other members of the Family Oleaceae have been documented as a source of medicinal substances since biblical times. Needless to say, many researchers have studied the cocktail of phytogenic substances produced by the olive and other members of the Family Oleaceae. One compound that has received attention from the research community is the secoiridoid glucoside oleuropein, a compound of the formula

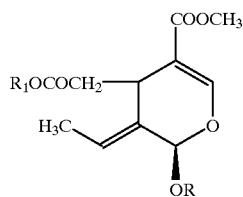

wherein R is glycosyl and $R_1$ is 2-(3,4-dihydroxyphenyl) ethyl. Related secoiridoids wherein $R_1$ is H, $CH_3$ or 2-(4-hydroxyphenyl ethyl) are also known to be endogenous to many plant species of the family Oleaceae, although in lesser concentrations and in fewer identified species than the ubiquitous oleuropein.

Animal studies have revealed that oleuropein itself or as a component of extracts of plant tissues containing that compound exhibit both hypoglycemic and cardiovascular effects. It is also known that oleuropein can be acid hydrolyzed to produce (−)-elenolic acid, a compound which has been reported to have antiviral properties in vitro, but little, if any, activity in vivo.

The present invention is based on the discovery that secoiridoid glucosides of the formula

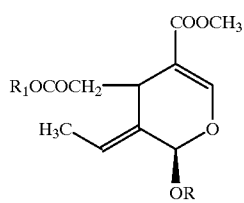

(I)

wherein R is glycosyl and $R_1$, is hydrogen or an ester-forming group are metabolized in vivo to the dextrorotatory form of elenolic acid [(+)-elenolic acid], a compound of the formula

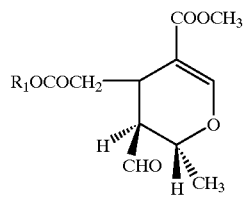

(II)

wherein $R_1$, is hydrogen, a compound which is believed to be more available in vivo than the corresponding diasteromer(−)-elenolic acid of the formula

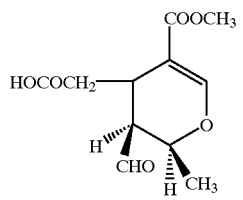

(III)

The enhanced in vivo efficacy of the oleuropein metabolite, (+)-elenolic acid relative to the corresponding levorotatory compound is thought to be due, at least in part, to its reduced affinity for serum proteins and thus its greater availability for uptake by virus infected tissues. Antivirally effective blood levels of (+)-elenolic acid can also be achieved by administration of (+)-elenolic acid and its esters of the formula

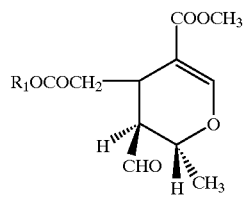

(II)

wherein $R_1$ is hydrogen or a pharmaceutically acceptable ester-forming group and salts thereof, which can be prepared from secoiridoid glucosides naturally occurring in plant material of the family Oleaceae via extraction and controlled enzyme (glucosidase) hydrolysis and/or deesterification/transesterification reactions.

Thus, it is one object of the present invention to provide a method of treatment of disease of viral origin in warm-blooded vertebrates by administering antiviral compositions containing secoiridoid glucosides native to the plant family Oleaceae and derivatives thereof.

Another object of the invention is to provide oral dosage forms of secoiridoid glucosides of *Olea europaea* and derivatives thereof.

In another more particular aspect of this invention plant material of the family Oleaceae and extracts thereof containing naturally occurring oleuropein glucosides and enzyme hydrolysates thereof are administered in treatment of diseases of viral origin in warm-blooded vertebrates suffering from such diseases.

One further object of this invention is a method for establishing antivirally effective blood levels of (+)-elenolic acid by the administration of oleuropein glucosides native to the family Oleaceae or their derivatives via transesterification, diesterification and/or glucolysis.

DETAILED DESCRIPTION OF THE INVENTION

The present invention is directed to a method of treatment of disease of viral origin in warm-blooded vertebrates and to pharmaceutical formulations for use in such treatment methods. The method comprises the step of administering to a vertebrate suffering from a disease of viral origin an antivirally effective amount of an antiviral composition comprising a compound of the formula

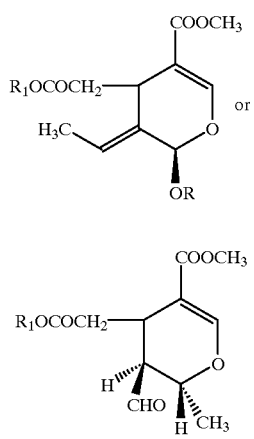

and a pharmaceutically acceptable carrier therefor. In the above formula, the group R is glucosyl and $R_1$, is hydrogen or a pharmaceutically acceptable ester-forming group. When $R_1$ is hydrogen, the acid compound represented can be utilized in the form of one of its pharmaceutically acceptable salts.

There are many diseases of viral etiology that afflict man and animal. In man, diseases such as hepatitis, mononucleosis, shingles, herpes, influenza, the common cold and even certain types of leukemia are known to be of viral etiology. Viral infections are also common in many animal species, both in meat producing and in companion animals. Rotovirus infections plague swine. Cattle develop bovine rhinovirus infections (shipping fever) when subjected to conditions of stress. Canine parvovirus and feline leukemia virus are common viral infections in those companion animals species. Such diseases of viral origin can be treated with resultant reduction in clinical symptomology by therapeutic administration of antiviral compositions in accordance with this invention.

The antiviral compositions administered in accordance with this invention comprise a compound of Formula I or II above in combination with a pharmaceutically acceptable carrier. The compounds of Formula I wherein $R_1$ is 2-(4-hydroxyphenyl)ethyl or 2-(3,4-dihydroxyphenyl)ethyl are naturally occurring compounds in many plants of the Family Oleaceae, including members of the genus Fraxinus, Syringa and the genus Ligustrum. Preferred plant sources of the naturally occurring secoiridoids of Formula I wherein $R_1$ is 2-(4-hydroxyphenyl)ethyl and 2-(3,4-dihydroxyphenyl) ethyl are varieties of Olea europaea (the olive). Preferred varieties of Olea europaea as a source of secoiridoid glycosides for use in accordance with this invention are the varieties Manzanillo and Mission.

The most prevalent of the secoiridoid compounds in such varieties is the compound of Formula I wherein $R_1$, is 2-(3,4-dihydroxyphenyl)ethyl and R is glucosyl, a compound given the common name oleuropein. That compound can be readily isolated from plant material, preferably ground leaves of the olive by aqueous or aqueous-alcoholic extraction at room temperature or above, preferably at elevated temperature of about 40 to about 100° C.

Oleuropein can then be purified, for example, by chromatographic separation procedures. That compound can then be used to formulate antiviral compositions in accordance with this invention or to prepare other antivirally effective compounds represented by Formulas I or II. Thus, for example, oleuropein can be subjected, to base catalyzed transesterification wherein the $R_1$, group 2-(3,4-dihydroxyphenyl)ethyl is exchanged with another pharmaceutically acceptable ester-forming group. The term "pharmaceutically acceptable ester-forming group" as used in defining the present invention, refers to those ester-forming groups which when cleaved via esterase reactions in vivo produce substantially non-toxic, physiologically compatible alcohols. Suitable pharmaceutically acceptable ester-forming groups include $C_1$–$C_8$ lower alkyl, and substituted $C_1$–$C_8$ alkyl, benzyl, substituted benzyl wherein the substituents are halo, $C_1$–$C_4$ alkoxy, $C_1$–$C_4$ acyloxy, and the like. The compound of Formula I wherein $R_1$, is hydrogen can be produced by esterase-mediated deesterification of oleuropein, typically in an aqueous medium at a pH between about 6 and about 8.5.

The compounds of Formula II are prepared from the corresponding compounds of Formula I by treatment with glucosidase, preferably that from the olive at a pH of about 4 to about 5. The compound of Formula II wherein $R_1$ is hydrogen is (+)-elenolic acid.

The compounds of Formula I or II wherein $R_1$ is hydrogen represent carboxylic acids and such acids can be used in accordance with this invention in the acid form or in the form of their pharmaceutically acceptable salts formed with organic bases or inorganic bases, such as ammonium, alkali or alkaline earth metal hydroxides, carbonates, bicarbonates, and the like. Bases useful in preparing such salts include sodium hydroxide, potassium hydroxide, ammonium hydroxide, and potassium carbonate. Of the salt forms, the potassium and sodium salts are particularly preferred.

The antiviral compositions of the present invention can be administered orally or parenterally in an antivirally effective amount to treat, i.e., reduce the symptoms, of diseases of viral origin. Oral dosage forms can be in a solid or liquid form and comprise an antivirally effective amount of a compound of Formula I or Formula II above and a pharmaceutically acceptable carrier. Such dosage forms can be formulated from pure compounds of Formula I or Formula II, or they can be formulated from ground plant materials of the family Oleaceae, preferably leaves of Olea europaea, or aqueous or aqueous alcoholic extracts thereof. Thus, for example, extraction of dried olive leaves with two volumes of a 12–15% ethanol/water solution for 10 days at room temperature provides an extract containing about 70 to about 250 mg of oleuropein per two ounces of the liquid extract. The extract itself can be administered orally as an antiviral composition in accordance with the method of treatment of the present invention, or aqueous or aqueous alcoholic (preferably methanol or ethanol) extracts can be spray-dried to provide a dry powder which can be formulated into oral dosage forms with other pharmaceutically acceptable carriers.

The solid oral dosage form compositions in accordance with this invention are prepared in a manner well known in the pharmaceutical art, and comprise at least one compound of Formula I or Formula II associated with at least one pharmaceutically acceptable carrier. In making such compositions, the compound of Formula I or Formula II, either in pure form or as a component of ground plant material or extracts thereof, are usually mixed, diluted or enclosed within a carrier. The carrier can be in a solid form, semi-solid or liquid material which acts as a vehicle, carrier or medium for the active ingredient. Alternatively, the carrier can be in the form of a capsule or other container to facilitate oral administration. Thus the solid oral dosage forms for administration in accordance with the method of this invention can be in the form of tablets, pills, powders or soft or hard gelatin capsules. Alternatively, the antiviral compositions in accordance with this invention for oral administration can be in liquid form wherein the pharmaceutically acceptable carrier is water or an aqueous alcoholic medium. The compositions for administration in the present method can also be formulated with other common pharmaceutically acceptable excipients, including lactose, dextrose, sucrose, sorbitol, mannitol, starches, gums, calcium silicate, microcrystalline cellulose, polyvinylpyrrolidone, methylcellulose, water, alcohol and the like. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. Further the compositions of the present invention can be formulated so as to provide quick, sustained or delayed release of the active ingredient after administration to the patient by employing procedures well known in the art.

Orally administered compositions are preferably formulated in unit dosage form with each dosage normally containing from about 30 to about 500 mg of a compound of the Formula I or Formula II, more typically about 100 to about 500 mg of such active compounds. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier/excipient. The preferred dosage levels of the compounds of Formula I/Formula II for treatment of viral infections in accordance with this invention depend on the route of administration, the nature of the active compound or combination of active compounds, and patient condition. When administered orally for treatment of viral disease, the compounds of Formula I or Formula II are administered at a dose of about 0.1 to about 15 mg/kg, more preferably about 0.2 to about 10 mg/kg of patient/animal body weight. In treatment of viral infections oral dosage forms in accordance with this invention can be administered 1 to 4 times a day, again depending on patient condition and the nature of the disease being treated.

Similar considerations bear on the dosage range for parenteral administration of compounds of Formula I or Formula II in treatment of viral infections in accordance with this invention. Parenteral doses are, however, typically lower than those required for antiviral efficacy via the oral route of administration. Thus, antiviral treatment can be achieved by parenteral administration of about 0.05 to about 3 mg/kg of patient/animal body weight. Parenteral formulations for use in accordance with the present invention are prepared using standard techniques in the art. They are commonly prepared as sterile injectable solutions, using a parenterally acceptable carrier such as isotonic saline solution or as a sterile packaged powder prepared for reconstitution with sterile buffer or isotonic saline prior to administration to a patient. The injectable formulation can contain from about 1 to 50 mg of a compound of Formula I or II per ml of formulation.

Administration of an antivirally effective amount of a composition comprising a compound of Formula I or Formula II and a pharmaceutically acceptable carrier in accordance with this invention produce antivirally effective blood levels of (+)-elenolic acid, a compound of the formula

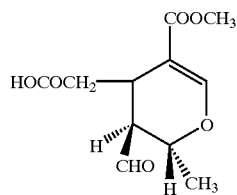

(IV)

via a heretofore unappreciated in vivo hydrolysis, and in the case of the compounds of Formula I, stereoselective hydrolysis/rearrangement. Administration of antiviral compositions of a compound of Formula I as part of ground/dried native plant material, preferably olive leaves, or as an aqueous or alcoholic extract of olive leaves is a particularly preferred embodiment in accordance with this invention. While not wishing to be bound by theory, the level of antiviral activity associated with such antiviral compositions may derive from a synergistic antiviral effect with other natural components of the olive leaf, such as the flavonoids rutin, hesperidin, and luteolin-7-glucoside.

The following non-limiting examples are illustrative of the method and compositions of the present invention. It is understood, however, that such examples are but representative of various embodiments of the invention and it is not intended that the invention be limited to the scope of the examples.

EXAMPLE 1

(A) A volume of dried leaves of *Olea europaea* is suspended in 2 volumes of red wine and held at room temperature for about 7 to about 10 days with periodic stirring. Filtration of the mixture provides a tincture containing about 88 mg of oleuropein per ounce of fluid.

(B) A volume of dried leaves of *Olea europaea* is suspended in two volumes of water and the resulting suspension is then subjected to conditions of high shear in a Waring blender to produce a dispersion of finely divided plant material which was held at a temperature of about 40 to about 65° for two days. Filtration of the mixture provides an aqueous extract containing about 72 mg of oleuropein per ounce of fluid. The aqueous extract is optionally blended with effective amounts of sweetening and/or flavoring agents to provide a palatable liquid oral dosage form of oleuropein.

(C) One volume of leaves or buds of *Olea europaea* is combined with about two volumes of a 3:2 mixture of methanol and water. The resulting aqueous alcoholic suspension of plant material is heated for 16 hours at about 75° C., cooled and filtered to provide an aqueous alcoholic extract. The extract is spray-dried to produce a powder comprising oleuropein. The powder is filled into gelatin capsules in an amount sufficient to provide 30 to about 500 mg of oleuropein per capsule.

(D) The spray-dried extract of (C) above is subjected to high pressure liquid chromatography to produce oleuropein [Formula I; R=glycosyl; $R_1$=2-(3,4-dihydroxyphenyl)ethyl]

and ligstroside [Formula I; R=glycosyl; $R_1$=2-(4-hydroxyphenyl)ethyl] in substantially pure form. The purified oleuropein is formulated alone or in combination with ligstroside with tabletting starch and a tabletting lubricant, magnesium stearate, to form a tabletting mixture. The tabletting mixture is pressed into compressed tablets containing about 30 to about 500 mg of oleuropein per tablet.

EXAMPLE 2

Oleuropein (1 g) is dispersed in 50 ml of methanol. The solution is cooled to about 10° C. and treated with stirring with about 2 g of potassium hydroxide pellets. The mixture is allowed to warm to room temperature and after about 6 hours, the reaction mixture is diluted with about 60 ml of 6 N HCl (pH about 7.5) and evaporated to dryness. The chromatographic purification of the product mixture provides oleoside [Formula I; R=glycosyl, $R_1$=methyl]. The purified oleoside is formulated into a solid oral dosage form containing about 250 mg of oleoside. Alternatively, oleoside is dissolved in sterile isotonic saline at a concentration of about 5 mg per ml to provide a parenteral dosage form for use in accordance with the method of this invention.

EXAMPLE 3

Five grams of oleuropein is dissolved in 500 ml of water buffered at pH 5.0 and treated with glucosidase until analysis of the reaction mixture by thin layer chromatography indicates completion of the reaction. Standard workup of the reaction mixture followed by chromatographic purification of the product mixture provides a compound of Formula II wherein $R_1$=2-(3,4-dihydroxyphenyl)ethyl. The purified product is formulated into oral or parenteral dosage forms and administered for treatment of viral diseases in accordance with the method of the present invention.

EXAMPLE 4

A solution of 500 mg of the product of Example 3 in 50 ml of water buffered at about pH 7.5 to about 8.5 is treated with commercially available esterase at a temperature of about 30° C. until thin layer chromatographic analysis of the esterase reaction mixture indicates completion of the reaction due to disappearance of the starting compound. After reaction completion, the pH of the mixture is readjusted to about 8.5 and after washing it twice with ethyl acetate, the pH of the solution is adjusted to about 4.5 in the presence of 30 ml of ethyl acetate. The ethyl acetate acid extract of the reaction mixture is separated, washed with distilled water and brine, and dried over anhydrous sodium sulfate. Evaporation to dryness provides (+)-elenolic acid [Formula II; $R_1$=hydrogen] in substantially pure form. The product is further purified by chromatography and/or crystallization as its sodium or potassium salt. It is formulated into oral or parenteral dosage forms in accordance with this invention for treatment of viral infections in warm-blooded vertebrates.

EXAMPLE 5

Dried leaves of *Olea europaea* are ground to a fine powder and loaded into gelatin capsules such that each capsule contains a volume of ground plant material containing between about 30 and about 500 mg of oleuropein per capsule. Dried olive leaves typically contain about 60 to about 90 mg of oleuropein per gram of dried leaf. The capsules are administered orally for treatment of diseases of viral origin in accordance with this invention.

EXAMPLE 6

The antiviral efficacy of a composition of Example 1(A) above was evaluated in treatment of six subjects afflicted with herpes virus infections. Each of the six subjects ingested two ounces of the formulation every six hours. All subjects reported reduction of herpetic lesions. Three subjects reported disappearance of lesions in 36–48 hours after initiating treatment. One subject, a 34 year old Caucasian female, had several months earlier discontinued use of birth control pills and it was thought that her estrogen surges were causing immunosuppression which complicated her infection. After three days of doubling the dosage of the tincture (four ounces every six hours) most of her lesions were resolved. Two other subjects, a male and a female, more recently infected were also given the higher doses (four ounces every six hours orally) and each reported improvement measured by reduction in severity of their herpetic lesions, and in at least one patient, a 22.8% decrease in antibody titers (IgG) three weeks after initiating therapy with the oleuropein-containing olive leaf extract.

I claim:

1. A method of treating a warm-blooded vertebrate suffering from a disease of viral origin, said method comprising the step of administering orally or parenterally to said vertebrate a therapeutically effective amount of an antiviral composition comprising a compound selected from the group consisting of oleuropein which is a compound of the formula

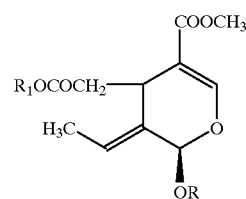

(I)

wherein $R_1$ is 2-(3,4-dihydroxyphenyl)ethyl and R is glucosyl, deesterified oleuropein of Formula I above wherein $R_1$ is hydrogen, pharmaceutically acceptable salts of deesterified oleuropein, and other esters of formula I wherein $R_1$ is derived from substantially non-toxic physiologically compatible alcohols, and a pharmaceutically acceptable carrier therefor.

2. The method of claim 1, wherein the compound is oleuropein.

3. The method of claim 1, wherein the disease of viral origin is selected from the group consisting of herpes mononucleosis, hepatitis, and diseases deriving from infection by rotovirus, bovine rhinovirus, canine parvovirus and feline leukemia virus.

* * * * *